(12) United States Patent
Phillips

(10) Patent No.: US 11,896,637 B1
(45) Date of Patent: Feb. 13, 2024

(54) SYSTEM AND PROCESS FOR EXTRACTING CANNABINOIDS

(71) Applicant: Joe Phillips, Plano, TX (US)

(72) Inventor: Joe Phillips, Plano, TX (US)

( * ) Notice: Subject to any disclaimer, the term of this patent is extended or adjusted under 35 U.S.C. 154(b) by 0 days.

(21) Appl. No.: 17/521,669

(22) Filed: Nov. 8, 2021

(51) Int. Cl.
*A61K 36/185* (2006.01)

(52) U.S. Cl.
CPC ........ *A61K 36/185* (2013.01); *A61K 2236/19* (2013.01); *A61K 2236/331* (2013.01)

(58) Field of Classification Search
None
See application file for complete search history.

(56) References Cited

FOREIGN PATENT DOCUMENTS

WO    WO 2021/168115    *    8/2021

* cited by examiner

*Primary Examiner* — Michael V Meller
(74) *Attorney, Agent, or Firm* — Richard Eldredge; Eldredge Law Firm

(57) ABSTRACT

A system and process for extracting cannabinoids from a marijuana or hemp plant, the system and process utilizing an aqueous solution containing one or more biocatalysts which act upon the marijuana or hemp plant matter to create cannabinoids.

1 Claim, 2 Drawing Sheets

SYSTEM AND PROCESS FOR EXTRACTING CANNABINOIDS

BACKGROUND

1. Field of the Invention

The present invention relates generally to systems and process for extracting cannabinoids from marijuana or hemp plant matter, and more specifically, to a system and process that utilizes biocatalysts for the extraction.

2. Description of Related Art

Systems and processes for extraction of cannabinoids are well known in the art. The extraction of cannabinoids allows for utilization of a marijuana or hemp plant in various ways. For example, a marijuana or hemp plant on its own is conventionally not considered useful, however, the plant contains over dozens of cannabinoids, which are considered the active ingredients that provide users with the desired side effect. The extraction of these cannabinoids can be costly, time consuming, and inefficient.

Accordingly, although great strides have been made in the area of cannabinoid extraction processes and systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
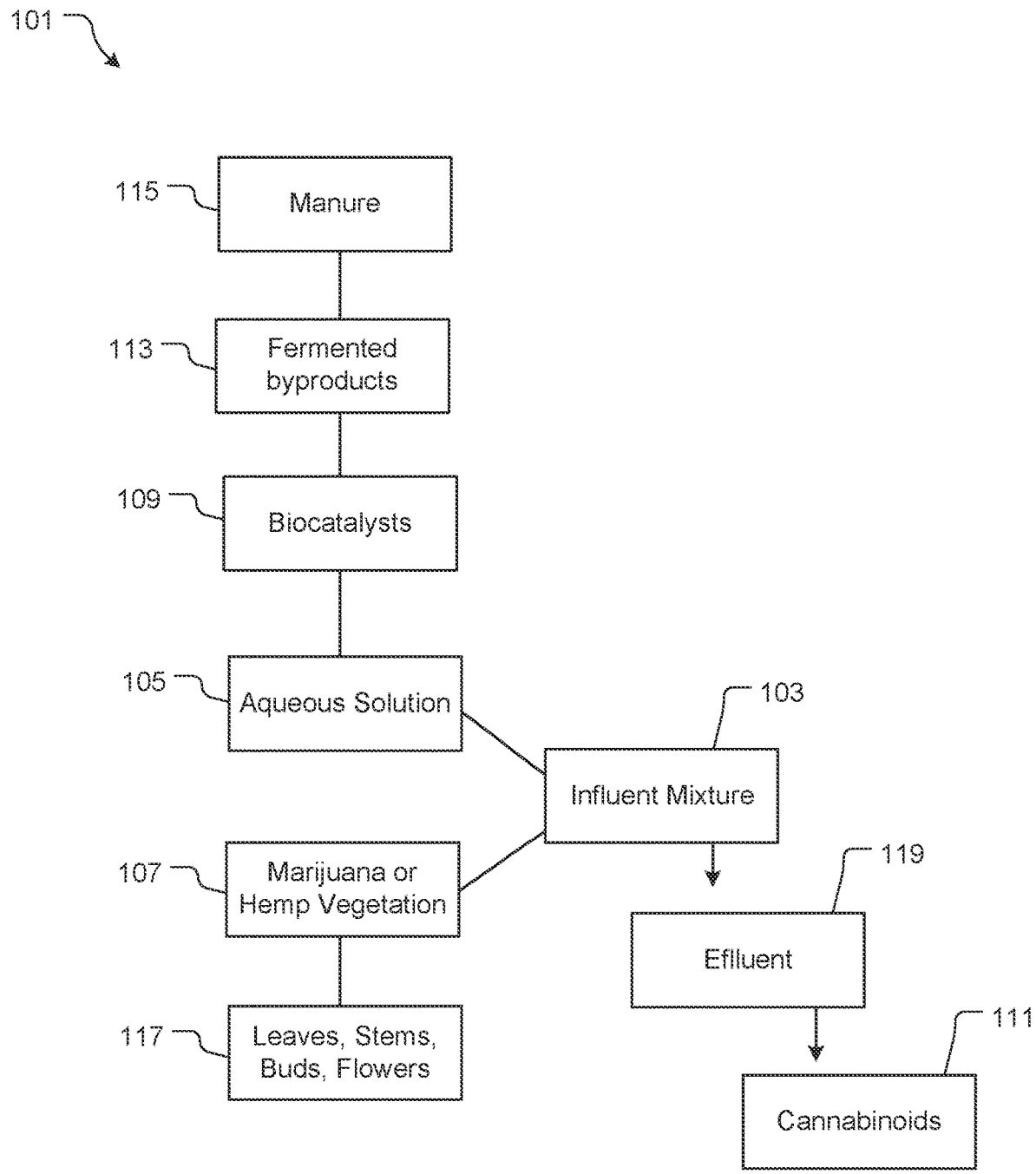
FIG. 1 is a schematic of a cannabinoid extraction system in accordance with the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional cannabinoid extraction systems. Specifically, the present invention provides for a novel and efficient means to extract cannabinoids, specifically utilizing an aqueous solution with biocatalysts. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a schematic of a cannabinoid extraction system 101 in accordance with a preferred embodiment of the present application. It will be appreciated that system 10 overcomes one or more of the above-listed problems commonly associated with conventional cannabinoid extraction systems.

In the contemplated embodiment, system 101 includes an influent mixture 103, which is created through mixing an aqueous solution 105 with marijuana or hemp vegetation 107. It should be appreciated that the aqueous solution 105 and the marijuana or hemp vegetation 107 will be mixed in predetermined amounts.

It should be appreciated that one of the unique features believed characteristic of the present application is the utilization of the aqueous solution 105. The aqueous solution of the present invention includes one or more biocatalysts 109, which are the active ingredient utilized to extract cannabinoids 111. It should be appreciated that the biocatalysts may be derived from various compositions, however, in the preferred embodiment, the biocatalyst 109 are derived specifically from a fermented byproduct 113, which may further be derived specifically from manure 115.

During implementation of system 101, the marijuana or hemp vegetation 107 may be selected from various plant parts 117 as would be known by those skilled in the art.

Once the influent mixture 103 is created, an effluent 119 byproduct will be available from which the cannabinoids 111 are extracted. The cannabinoids 111 are then utilized as desired by the user.

Figure 2:
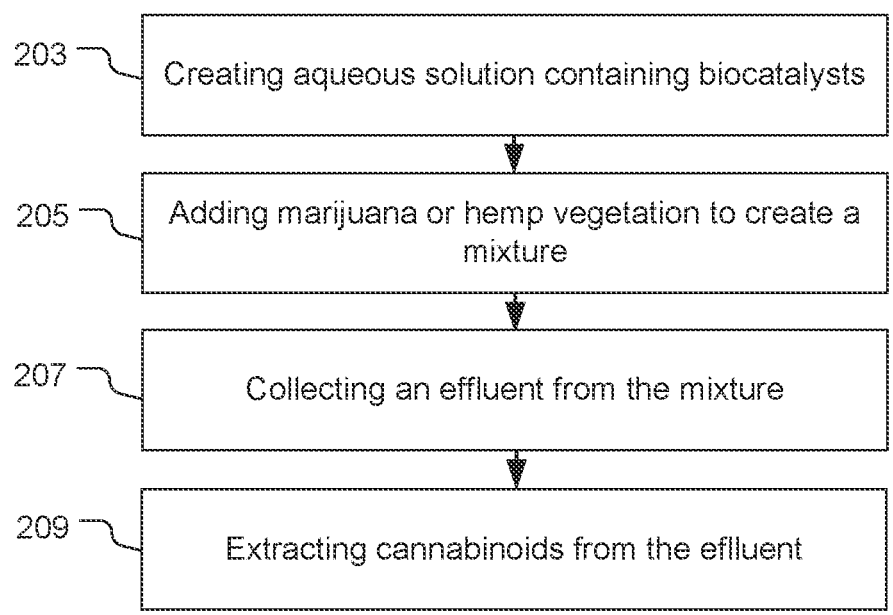
FIG. 2 is a flowchart of a cannabinoid extraction process in accordance with the present application.

In FIG. 2, a flowchart 201 depicts a process of cannabinoid extraction in accordance with the present invention. First, the aqueous solution containing one or more biocatalysts is created, as shown with box 203. To this solution, the marijuana or hemp vegetation is added to create the mixture, as shown with box 205. From the mixture, an effluent is collected, as shown with box 207. The cannabinoids can then be extracted from the effluent, as shown with box 209.

It should be appreciated that the biocatalysts act upon the marijuana or hemp vegetation to provide for extraction of the cannabinoids therefrom.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A process of extracting cannabinoids from hemp using manure consisting essentially of:
   a. creating an aqueous solution of manure;
   b. adding hemp to the aqueous solution of manure to create a mixture of manure;
   c. collecting an effluent from the mixture of manure; and
   d. extracting an amount of cannabinoids from the effluent.

\* \* \* \* \*